United States Patent
Pagani et al.

(10) Patent No.: US 6,340,451 B1
(45) Date of Patent: Jan. 22, 2002

(54) METHOD FOR THE SIMULTANEOUS MODERNIZATION OF A PLANT FOR AMMONIA PRODUCTION AND A PLANT FOR UREA PRODUCTION

(75) Inventors: Giorgio Pagani, Lugano; Federico Zardi, Breganzona, both of (CH)

(73) Assignee: Ureaecasale S.A., Lugano-Besso (CH)

( * ) Notice: Subject to any disclaimer, the term of this patent is extended or adjusted under 35 U.S.C. 154(b) by 0 days.

(21) Appl. No.: 09/538,971

(22) Filed: Mar. 31, 2000

(30) Foreign Application Priority Data

Mar. 31, 1999 (EP) ............................................. 99201009

(51) Int. Cl.$^7$ .......................... C01C 1/04; C07C 273/00
(52) U.S. Cl. ..................... 423/359; 422/189; 422/234; 564/69; 564/70
(58) Field of Search ........................... 423/359; 564/66, 564/67, 69, 70, 71, 72, 73; 422/234, 189

(56) References Cited

U.S. PATENT DOCUMENTS

| | | | |
|---|---|---|---|
| 3,349,126 A | 10/1967 | Hsu | 260/555 |
| 4,138,434 A | 2/1979 | Lagana et al. | 260/555 |
| 4,235,816 A | 11/1980 | Lagana et al. | 562/555 |
| 4,320,103 A | 3/1982 | Pagani | 423/359 |
| 6,231,827 B1 * | 5/2001 | Pagani et al. | 423/359 |

FOREIGN PATENT DOCUMENTS

EP  0 624 571  11/1994  ......... C07C/273/04

* cited by examiner

*Primary Examiner*—Steven P. Griffin
*Assistant Examiner*—Maribel Medina
(74) *Attorney, Agent, or Firm*—Sughrue Mion, PLLC (57) ABSTRACT

A method for the simultaneous modernization of a plant for ammonia synthesis and a plant for urea synthesis, provides—inter alia—the arrangement of a carbamate synthesis section and a carbamate decomposition section, in order to obtain a predetermined amount of carbamate in aqueous solution and of hydrogen and nitrogen in gaseous phase which are fed to the existing sections for urea synthesis, respectively ammonia synthesis. Thanks to this method of modernization it is possible to remarkably increase the production capacity and at the same time to reduce the energy consumption of the urea and ammonia plants without being forced to replace or anyway overload the existing sections of decarbonation, methanation and compression, in general.

22 Claims, 3 Drawing Sheets

METHOD FOR THE SIMULTANEOUS MODERNIZATION OF A PLANT FOR AMMONIA PRODUCTION AND A PLANT FOR UREA PRODUCTION

FIELD OF APPLICATION

The present invention relates to a method for the simultaneous modernisation of a plant for ammonia production and of a plant for urea production.

More specifically, the invention relates to the simultaneous modernisation of a plant for ammonia production of the type comprising a section for the production of raw ammonia synthesis gas, which comprises carbon monoxide, hydrogen and nitrogen, a carbon monoxide conversion section, a decarbonation section, a methanation section, a compression section of the ammonia synthesis gas and an ammonia synthesis section, provided in series, and a plant for urea production of the type comprising a carbon dioxide compression section, a urea synthesis section and a urea recovery section, provided in series.

In the following description and enclosed claims, by the term "modernisation", it is intended to mean the modification of a pre-existing plant with the purpose of improving its performance and obtaining, for example, an increase of the production capacity and/or of the conversion yield as well as a reduction of the energy consumption.

In particular, in this case, by the term "simultaneous modernisation", it is intended to mean a modernisation that concerns at the same time both an existing plant for ammonia production and an existing plant for urea production, in order to increase the production capacity thereof, while maintaining the main equipment of the high pressure synthesis sections (synthesis loop) as well as of the decarbonation, methanation and compression sections in general.

According to a further aspect thereof, the present invention relates also to a process for the combined production of ammonia and urea as well as to a plant for implementing such process.

The present invention has specific application in those cases wherein the ammonia plant and the urea plant are intimately correlated between each other, that is when all or anyway the greatest portion of the ammonia produced is converted into urea, making it react with the carbon dioxide obtained as by-product in the preparation of the ammonia synthesis gas.

As known, with respect to the production of ammonia and urea, the need of having on one hand plants of ever increasing capacity and operation efficiency and on the other hand ever lower investment and operation costs as well as lower energy consumption, is felt more and more.

PRIOR ART

To this end, methods have been proposed in the field, for the modernisation of existing plants both for ammonia and urea production substantially based on the modification of the synthesis reactor, on the replacement of the apparatuses upstream and/or downstream of the synthesis reactor with apparatuses of greater capacity and/or on the additional provision of new apparatuses in parallel to the existing apparatuses.

For example, in EP-0 202 454 a method is disclosed for the modernisation of a reactor for ammonia synthesis, whose catalytic beds are transformed from the axial type to the axial/radial type with an ensuing increase of the conversion yield of the reactor and therefore of the production capacity of the ammonia plant.

On the other hand, in EP-A-0 796 244 a method of modernisation of a plant for urea production is disclosed, which foresees the addition of a partial decomposition step of the carbamate in aqueous solution recycled to the synthesis reactor. With this method of modernisation, it is possible to remarkably reduce the amount of water recycled to the synthesis reactor, thus permitting to obtain an increase of the conversion yield and therefore of the production capacity of the plant.

One of the main problems that is encountered when a simultaneous increase of production capacity is considered in existing plants for ammonia and urea production, which are correlated to each other, is that of increasing accordingly the capacity of the sections upstream of the respective synthesis reactors.

In particular, the decarbonation, methanation and compression section of the ammonia synthesis gas as well as the compressors of the refrigeration cycles within the synthesis loop of ammonia and the compression section of the flow comprising carbon dioxide fed to the urea synthesis section are bottlenecks for the capacity increases, in that they are rapidly overloaded by the unavoidable increases of the flow rates of the reactants.

This problem is more serious when the existing plants have already being submitted to modernization according to the prior art and therefore the aforementioned sections or apparatuses are already at their operating limits.

In these cases, the methods of modernization according to the prior art only propose the replacement of the existing apparatuses with apparatuses of greater capacity or the addition in parallel of new apparatuses to the existing apparatuses, so as to increase the overall capacity of the various sections upstream of the respective synthesis reactors.

These provisions have a very bad impact both on the investment costs and on the energy consumption; furthermore the implementation of the methods of modernisation according to the prior art can be very complex.

Notwithstanding the ever increasing interest in the industry of modifying the existing plants—instead of realising new plants—in order to increase the production capacity and decrease the energy consumption with minimum investments, because of the aforesaid disadvantages, the modernisation of the plants for ammonia and urea production implies to date high investments, sometimes even comparable to those required for building new plants. Furthermore, with the methods of modernisation according to the prior art, the increase of production capacity is generally achieved to prejudice of the conversion yield, and therefore with greater energy consumption.

SUMMARY OF THE INVENTION

The technical problem underlying the present invention is that of providing a method for the simultaneous modernisation of a plant for ammonia production and a plant for urea production that provides for an increase of the respective production capacities and implies low energy consumption at low investment costs and is technically easy to implement.

According to the present invention, this problems is solved by a method of the above indicated type that is characterised in that it comprises the steps of:

providing a carbamate synthesis section and a carbamate decomposition section;

providing means for feeding a suitably compressed raw ammonia synthesis gas flow comprising carbon dioxide, hydrogen and nitrogen to the carbamate synthesis section;

providing means for feeding a portion of a flow comprising ammonia, hydrogen and nitrogen obtained in the ammonia synthesis section to the carbamate synthesis section;

providing means for feeding at least part of a flow comprising carbamate in aqueous solution coming from the urea recovery section to the carbamate decomposition section;

providing means for feeding a flow comprising ammonia and carbon dioxide in vapour phase obtained in the decomposition section to the urea synthesis section;

providing means for feeding a flow comprising diluted carbamate in aqueous solution obtained in the carbamate decomposition section to the carbamate synthesis section;

providing means for feeding a gas flow comprising hydrogen and nitrogen obtained in the carbamate synthesis section to the ammonia synthesis section;

providing means for feeding a flow comprising carbamate in aqueous solution obtained in the carbamate synthesis section to the carbamate decomposition section and/or to urea synthesis section.

Advantageously, the present invention allows to increase remarkably the production capacity of the ammonia, respectively urea plant, realising in a simple and effective way a partial integration between the two plants and accordingly achieving a debottlenecking of the existing apparatuses upstream of the respective synthesis sections which are substantially not involved in the capacity increase.

In other words, thanks to the step of providing additional sections of carbamate synthesis and decomposition suitably connected to the existing sections of the ammonia and urea plants, it is possible to increase the production capacity of such plants without being forced to increase the flow rate of the reactants flowing through the decarbonation, methanation and compression sections that may then operate optimally.

In fact, the amount of reactants necessary for obtaining the desired increase of production capacity of ammonia and urea may advantageously be produced in the additional sections of carbamate synthesis and decomposition that are independent from the existing sections of decarbonation, methanation and compression.

In particular, as it will appear more clearly in the following description with reference to the drawings, thanks to the carbamate synthesis section, a gas flow is obtained which comprises hydrogen and nitrogen as additional reactants for ammonia synthesis, whereas thanks to the carbamate decomposition section a gas flow is obtained comprising ammonia and carbon dioxide as additional reactants for urea synthesis.

A further advantage resulting from the method of modernization according to the present invention is given by the fact that, by providing the additional carbamate decomposition section for submitting to a treatment of partial decomposition at least one portion of the carbamate flow in aqueous solution resulting from the urea recovery section, it is possible to supply to the carbamate synthesis section a solution with a high content of water and at the same time to supply to the urea synthesis reactor a flow comprising ammonia and substantially anhydrous carbon dioxide, that permits to decrease the molar ratio $H_2O/CO_2$ in such reactor and therefore to increase the conversion yield of urea.

Accordingly, this feature is advantageous, not only because of the increase of production capacity of the urea plant but also because of the remarkable reduction of the energy consumption together with the increase of the conversion yield.

Further on, in doing so, it is possible not only to maintain a low $H_2O/CO_2$ molar ratio in the urea synthesis reactor, but also to exploit advantageously at least part of the water contained in the carbamate flow in aqueous solution coming out from the urea recovery section, recycling it in an easy and economic way to the carbamate synthesis section in order to enhance the absorption of the carbon dioxide, so as to obtain and maintain the carbamate produced in aqueous solution, thus avoiding an undesired crystallization of the same.

According to a further aspect thereof, the present invention relates to a process for the combined production of ammonia and urea in a plant of the type comprising a section for the production of raw ammonia synthesis gas comprising carbon monoxide, hydrogen and nitrogen, a carbon monoxide conversion section, a decarbonation section, a methanation section, a compression section for the ammonia synthesis gas, an ammonia synthesis section, a carbon dioxide compression section, a urea synthesis section and a urea recovery section, the process being characterised in that a first portion of ammonia and urea is produced through the steps of:

flowing a flow of raw ammonia synthesis gas comprising carbon dioxide, hydrogen and nitrogen through the sections of decarbonation, methanation and compression of the synthesis gas, obtaining a suitably compressed gas flow comprising hydrogen and nitrogen;

feeding the suitably compressed gas flow comprising hydrogen and nitrogen to the ammonia synthesis section;

feeding a portion of the ammonia obtained in the ammonia synthesis section together with the carbon dioxide coming out from the decarbonation section to the urea synthesis section;

whereas a second portion of ammonia and urea is produced through the steps of:

submitting at least part of a flow comprising carbamate in aqueous solution coming from the urea recovery section to a treatment of partial decomposition in a carbamate decomposition section, thus obtaining a flow comprising ammonia and carbon dioxide in vapour phase and a flow comprising diluted carbamate in aqueous solution;

feeding the flow comprising ammonia and carbon dioxide in vapour phase to the urea synthesis section;

feeding the flow comprising diluted carbamate in aqueous solution resulting from the treatment step to a carbamate synthesis section;

feeding a suitably compressed raw ammonia synthesis gas flow comprising carbon dioxide, hydrogen and nitrogen to the carbamate synthesis section;

feeding a portion of a flow comprising ammonia, hydrogen and nitrogen obtained in the ammonia synthesis section to the carbamate synthesis section;

reacting ammonia with carbon dioxide in the carbamate synthesis section, obtaining a flow comprising carbamate in aqueous solution and a gas flow comprising hydrogen and nitrogen;

feeding the flow comprising carbamate in aqueous solution to the carbamate decomposition section and/or to the urea synthesis section;

feeding the gas flow comprising hydrogen and nitrogen to the ammonia synthesis section.

The present invention relates also to a plant intended for implementing the aforesaid process for the combined production of ammonia and urea that is characterised in that it comprises:

a section for the production of raw ammonia synthesis gas comprising carbon monoxide, hydrogen and nitrogen, a carbon monoxide conversion section, a decarbonation section, a methanation section, a compression section of ammonia synthesis gas, an ammonia synthesis section, a carbon dioxide compression section, a urea synthesis section, a urea recovery section, a carbamate synthesis section and a carbamate decomposition section;

means for feeding a suitably compressed raw ammonia synthesis gas flow comprising carbon dioxide, hydrogen and nitrogen to the carbamate synthesis section;

means for feeding a portion of a flow comprising ammonia, hydrogen and nitrogen obtained in the ammonia synthesis section to the carbamate synthesis section;

means for feeding at least part of a flow comprising carbamate in aqueous solution coming from the urea recovery section to the carbamate decomposition section;

means for feeding a flow comprising ammonia and carbon dioxide in vapour phase obtained in the decomposition section to the urea synthesis section;

means for feeding a flow comprising diluted carbamate in aqueous solution obtained in the carbamate decomposition section to the carbamate synthesis section;

means for feeding a gas flow comprising hydrogen and nitrogen obtained in the carbamate synthesis section to the ammonia synthesis section;

means for feeding a flow comprising carbamate in aqueous solution obtained in the carbamate synthesis section to the carbamate decomposition section and/or to urea synthesis section.

According to the invention, the plants intended for implementing the process for the simultaneous production of ammonia and urea can be realised both ex-novo and—preferably—by modifying existing plants so as to obtain an increase of the production capacity thereof and an improved performance with respect to the energy consumption.

Further features and advantages of the present invention will appear more clearly from the following non limitative description of an embodiment of the method of modernisation, respectively of the urea synthesis process according to the invention, made with reference to the attached drawings.

DETAILED DESCRIPTION OF A PREFERRED EMBODIMENT

Figure 1:
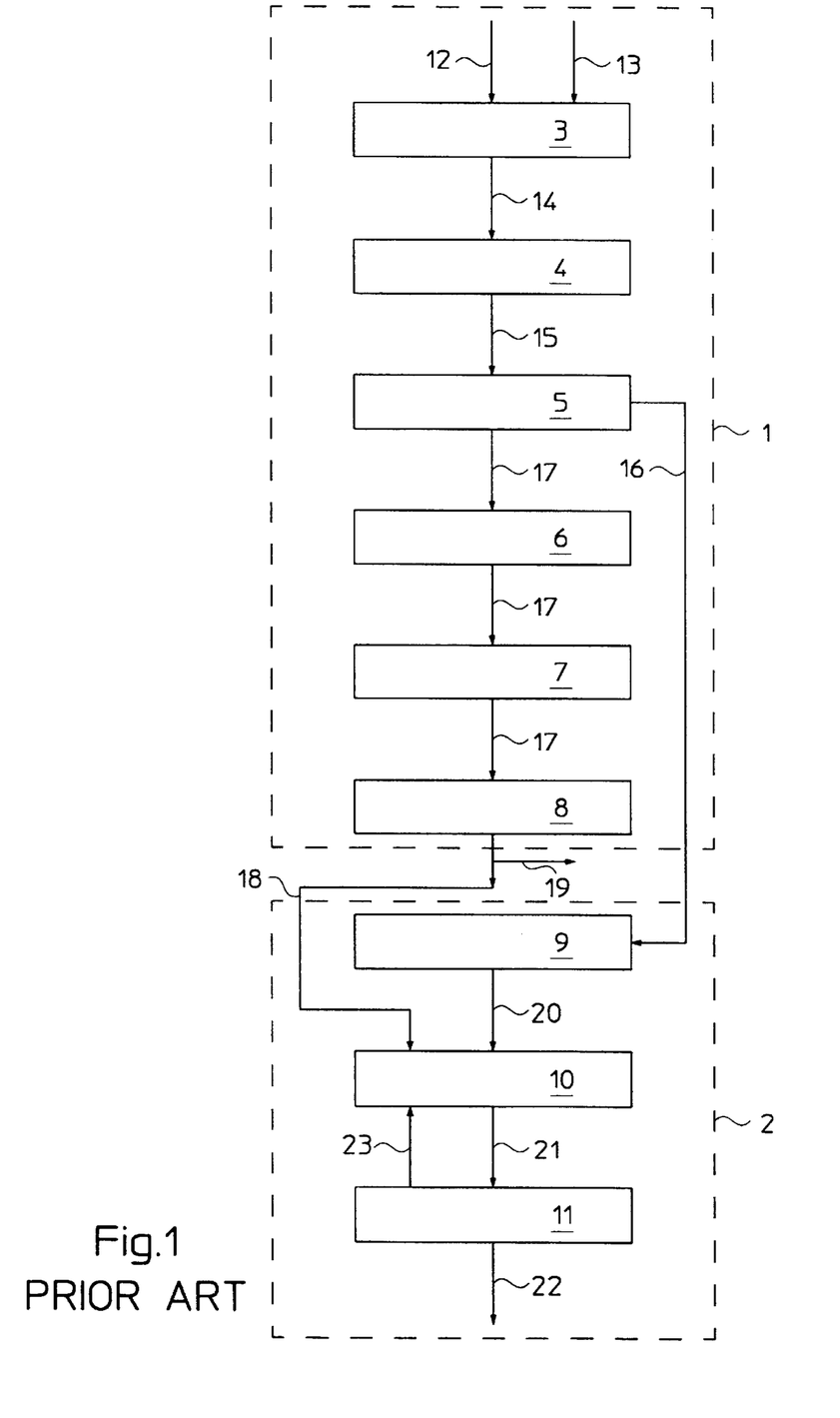
FIG. 1 shows a block diagram representing a plant for ammonia production and a plant for urea production, correlated to each other, according to the prior art.

In FIG. 1 a plant for ammonia production generally indicated with 1 and a plant for urea production generally indicated with 2 of a conventional type are represented in their main items.

Plant 1 for ammonia production and plant 2 for urea production are conventionally correlated to each other in that at least part of the ammonia produced and of the carbon dioxide obtained in the ammonia plant are used as reactants in the urea plant.

Plant 1 for ammonia production comprises, provided in series, a section 3 for the production of raw ammonia synthesis gas comprising carbon monoxide, hydrogen and nitrogen, a section 4 of conversion of the carbon monoxide, a section 5 of decarbonation, a section 6 of methanation, a section 7 of compression of the ammonia synthesis gas and a section 8 for ammonia synthesis.

Plant 2 for urea production comprises, provided in series, a section 9 of compression of carbon dioxide, a section 10 for urea synthesis and a section 11 of urea recovery.

At inlet to the section 3, through respective suitable means 12 and 13, there is fed a gas flow comprising hydrocarbons and steam and a gas flow comprising nitrogen, for example air or air enriched in oxygen, respectively.

Such feeding means comprises, for example, pipelines or connecting ducts, pumps, compressors, ejectors, and other apparatuses of known type, that are generally employed in such kind of plants, and therefore will not be further described in the following description.

Generally speaking, in the present description and in the following claims, and except from where explicitly noted, by the term "feeding means" it is intended to mean pipelines, connecting lines, pumps, compressors, ejectors or other devices of known type, which are used for transporting a liquid or gaseous flow from a location to another one in the plant.

The term "hydrocarbons", is used to indicate generically a raw material source of hydrogen and carbon, such as for example methane, or a mixture of liquid and/or gaseous hydrocarbons such as natural gas and naphtha. Whereas the term "air enriched in oxygen" is meant to indicate air with a molar content of oxygen higher than 21%, for example comprised between 22 and 80%.

The section 3 comprises generally a primary reforming step wherein a first decomposition with steam of the hydrocarbons takes place, with the formation of hydrogen, carbon monoxide and carbon dioxide, and a secondary reforming step wherein the decomposition is made proceed with the addition of the gas flow comprising nitrogen.

At outlet from section 3, a raw ammonia synthesis gas flow is obtained which comprises carbon monoxide, hydrogen and nitrogen that is fed to the section 4 of conversion of the carbon monoxide through suitable means 14.

Anyway, in view of the purposes of this invention, the raw ammonia synthesis gas flow comprising hydrogen, nitrogen and carbon monoxide may be produced in section 3 with any other known technique, as an alternative to the steam reforming of the hydrocarbons, for example, through a simple step of partial catalytic oxidation with addition of enriched air.

The section 4 may comprise a high temperature conversion step and a low temperature conversion step for the conversion into carbon dioxide of the carbon monoxide present in the raw ammonia synthesis gas flow.

The raw ammonia synthesis gas flow coming out of the section 4 is supplied—through means 15—to the section 5 of decarbonation wherein the carbon dioxide is suitably separated from the ammonia synthesis gas flow and fed—through means 16—to the compression section 9.

The ammonia synthesis gas flow comprising hydrogen and nitrogen coming out from the decarbonation section 5 before being fed in the ammonia synthesis section 8 is made to flow through means 17 through the methanation section 7 and a compression section 8 of conventional type, wherein the gas flow is suitably purified and compressed.

In particular, in the methanation section 7, possible traces of carbon monoxide and/or carbon dioxide are suitably transformed in methane. In the compression section, the so purified gas flow is then compressed at the synthesis pressure generally comprised between 100 and 200 bar.

The operative conditions of pressure and temperature inside and through the sections 3–8 are equal to the typical conditions of a conventional plant for ammonia synthesis, well known to the person skilled in the art.

The synthesis loop at high pressure defined by the section 8 generally comprises a reactor for ammonia synthesis and suitable means and apparatuses for the separation and recycling of the unreacted hydrogen and nitrogen to the synthesis reactor. These apparatuses further comprise the compressors of the refrigeration cycle.

The flow which comprises substantially ammonia, coming from the section 8, can be fed in its whole—through means 18—to the section 10 for urea synthesis or, according to the demands, a (even remarkable) portion thereof can be extracted directly from the plant 1 through means 19 for the most various uses. Should the production of urea be not required, the ammonia produced in the section 8 is therefore totally extracted from the plant 1 through means 19.

The gas flow comprising carbon dioxide, once suitably compressed in the section 9 is fed to the section 10 through means 20 and reacted with ammonia obtaining a reaction mixture comprising urea, carbamate and free ammonia in aqueous solution.

The high pressure and temperature synthesis loop defined by the section 11 generally comprises one or more reactors for urea synthesis and possibly—according to the type of process—one or more stripping and condensation unit.

The so obtained reaction mixture is fed—through means 21—to the urea recovery section 11, wherein the urea produced in the section 10 is separated from carbamate and liquid ammonia in aqueous solution and comes out of the plant 2 through means 22, upon having been further concentrated in a suitable section which is not shown.

The urea recovery section comprises in general one or two medium pressure (about 18 abs bar), respectively medium and low pressure (about 4 abs bar) carbamate decomposers, and respective carbamate condensers.

Carbamate and free ammonia in aqueous solution resulting from the urea recovery section 11 are finally recycled—through feeding means 23—to the urea synthesis section 10. It is worth noting that the recycle flow fed to the urea synthesis section 10 is particularly rich in water, which prejudice of the conversion yield in such section.

Figure 2:
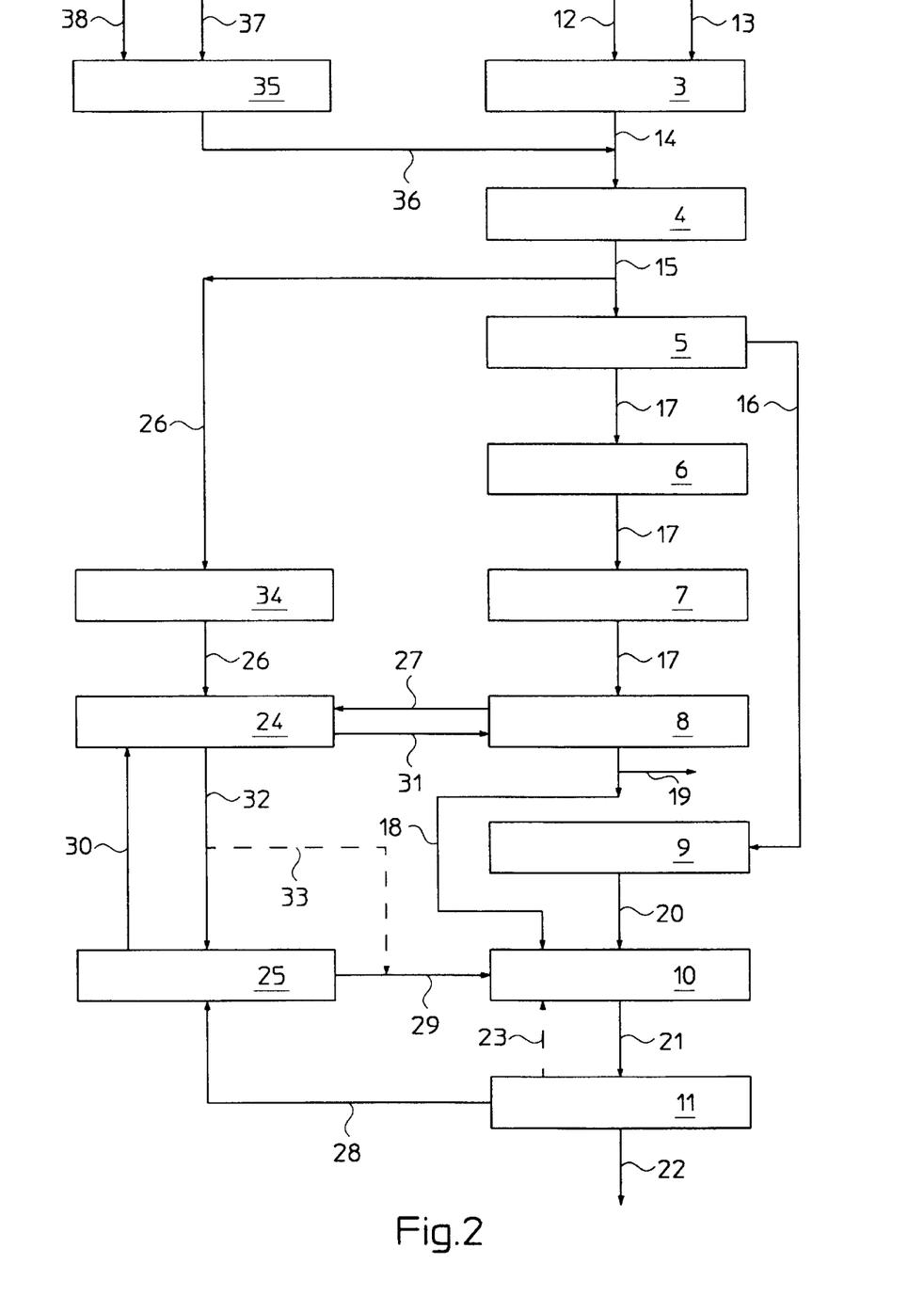
FIG. 2 shows a block diagram representing a plant for the simultaneous production of ammonia and urea resulting from the modernisation of the plants of FIG. 1 according to an embodiment of the present invention.

With reference to FIG. 2, a block diagram is advantageously indicated, representing a plant for the simultaneous production of ammonia and urea resulting from the modernisation of the plants of FIG. 1 according to an embodiment of this invention.

In FIG. 2, the details of the plants 1 and 2 of FIG. 1, structurally and functionally equivalent to those illustrated in FIG. 1 will be indicated with the same numerals and will not be described in the following any more.

Thanks to the present method of modernisation, it is possible to increase the production capacity of the plants 1 and 2 without overloading the sections upstream of the synthesis sections 8 and 10, in particular the sections 5–7 and 11 as well as the compressors of the refrigeration cycle provided in section 8.

To this end, according to an embodiment of the invention, the following sections and means are advantageously provided, independently from the order hereinbelow reported a carbamate synthesis section 24;

a carbamate decomposition section 25;

means 26 for feeding a suitably compressed raw ammonia synthesis gas flow comprising carbon dioxide, hydrogen and nitrogen to the carbamate synthesis section 24;

means 27 for feeding a portion of a flow comprising ammonia, hydrogen and nitrogen obtained in the ammonia synthesis section 8 to the carbamate synthesis section 24;

means 28 for feeding at least part of a flow comprising carbamate in aqueous solution coming from the urea recovery section 11 to the carbamate decomposition section 25;

means 29 for feeding a flow comprising ammonia and carbon dioxide in vapour phase obtained in the decomposition section 25 to the urea synthesis section 10;

means 30 for feeding a flow comprising diluted carbamate in aqueous solution obtained in the carbamate decomposition section to the carbamate synthesis section 24;

means 31 for feeding a gas flow comprising hydrogen and nitrogen obtained in the carbamate synthesis section to the ammonia synthesis section 8; and means 32 for feeding a flow comprising carbamate in aqueous solution obtained in the carbamate synthesis section 24 to the carbamate decomposition section 25.

In this way, possible increases of production capacity of the plants for ammonia, respectively urea production are advantageously obtained by partially integrating the existing plants, without having to overload the existing sections of decarbonation, methanation and compression (including the compressors of the refrigeration cycle of the ammonia synthesis section) that generally already operate at their load limits and that are an obstacle to the aforementioned capacity increases.

In other words, thanks to the method of modernisation according to the invention, the additional amount of ammonia and urea intended to be produced in the existing plants, is obtained employing in the synthesis sections 8 and 10 corresponding amounts of reactants, that, however, are not obtained in the above described conventional way with reference to FIG. 1, but advantageously, through the following steps:

submitting at least part of the flow comprising carbamate in aqueous solution coming from the urea recovery section 11 (means 28) to a treatment of partial decomposition in a carbamate decomposition section 25, thus obtaining the flow (29) comprising ammonia and carbon dioxide in vapour phase and of the flow (30) comprising diluted carbamate in aqueous solution;

feeding the flow (29) comprising ammonia and carbon dioxide in vapour phase to the urea synthesis section 10;

feeding the flow (30) comprising diluted carbamate in aqueous solution resulting from the treatment step to the carbamate synthesis section 24;

feeding the suitably compressed raw ammonia synthesis gas flow (26) comprising carbon dioxide, hydrogen and nitrogen to the carbamate synthesis section 24;

feeding a portion of the flow comprising ammonia, hydrogen and nitrogen obtained in the ammonia synthesis section 8 (means 27) to the carbamate synthesis section 24;

reacting ammonia with carbon dioxide in the carbamate synthesis section 24, obtaining the flow (32) comprising carbamate in aqueous solution and the gas flow (31) comprising hydrogen and nitrogen;

feeding the flow (32) comprising carbamate in aqueous solution to the carbamate decomposition section 25; and feeding the gas flow (31) comprising hydrogen and nitrogen to the ammonia synthesis section.

The additional amounts of the reactants for ammonia, respectively urea synthesis are thus supplied to the sections 8, respectively 10, through means 31 and 29.

In doing so, it is evident how with this method of modernisation it is not necessary to use or potentiate the existing sections of decarbonation, methanation or compression which will be able to operate at their optimum with low energy consumption. Furthermore, the method according to the invention does not require even the addition of new sections of this type, that are very demanding in terms of energy consumption and expensive in terms of investment costs.

Particularly satisfying results in terms of investment costs and energy consumption have been achieved by providing the sections and additional means which were described above with reference to FIG. 2, in such a way to obtain an amount of reactants such to achieve an increase of ammonia, respectively urea production comprised between 10% and 50%, preferably between 30% and 45% with respect to the production before the modernisation.

Furthermore, had the existing plants 1 and 2 already been modernised or should they anyway operate with sections of decarbonation, methanation and compression generally at their load limits, the method according to the invention enables advantageously to share such load with the additional sections thus unloading the existing sections that will thus be able to operate at their optimum. In this way the energy consumption will be further reduced.

In order to maximise the conversion yield in the urea synthesis section 10 (reducing the $H_2O/CO_2$ molar ratio) and therefore to minimise the energy consumption in such section, it is preferable to send—through means 32—all the flow comprising carbamate in aqueous solution obtained in section 24 to the carbamate decomposition section 25.

The same applies to the flow comprising carbamate in aqueous solution coming from the urea recovery section 11, which will preferably be sent in its whole to the carbamate decomposition section 25.

As alternative, it is anyway foreseen the possibility to supply directly to the urea synthesis section 10—through means 33 (indicated in FIG. 2 with a dashed line)—all or anyway a portion of such flow comprising carbamate as well as—through means 23 (indicated in FIG. 2 with a dashed line)—part of the flow comprising carbamate in aqueous solution.

Advantageously, the raw ammonia synthesis gas flow comprising carbon dioxide, hydrogen and nitrogen is fed through the means 26 to the carbamate synthesis section 24 suitably compressed, that is to say at a pressure substantially equivalent to the operating pressure of the section 24 that corresponds to the pressure in the ammonia synthesis section 8.

To this end, according to a preferred embodiment of the present method of modernisation, the further steps are foreseen of providing an additional compression section 34 and means 26 for feeding the raw ammonia synthesis gas flow comprising carbon dioxide, hydrogen and nitrogen, to the additional compression section 34 and from this to the carbamate synthesis section.

The compression section 34 may comprise one or more compression units of conventional type that enable the suitable compression both of the additional reactants for ammonia synthesis and of the additional amount of carbon dioxide for urea synthesis.

According to the embodiment of this method of modernisation shown in FIG. 2, the means 26 for feeding the raw ammonia synthesis gas comprising carbon dioxide, hydrogen and nitrogen to the carbamate synthesis section 24 comprises means (not shown, for example control valves) for extracting one portion of the raw ammonia synthesis gas flow coming out of the carbon monoxide conversion section 4 and delivered through means 15 to the decarbonation section 5.

In other words, the gas flow comprising carbon dioxide, hydrogen and nitrogen to be delivered to the carbamate synthesis section 24 is in this case advantageously extracted upstream of the decarbonation section 5.

In doing so, the gas flow to be delivered to section 24 has already been partially compressed in the carbon monoxide conversion section 4 thus reducing the energy consumption necessary for compressing it to the required pressure. It is worth noting how this is an advantage both for the flow of reactants to be delivered to the ammonia synthesis section 8 and for the flow of carbon dioxide to be delivered to the urea synthesis section 10.

To this respect, particularly satisfying results have been obtained with the portion of the raw ammonia synthesis gas flow comprising carbon dioxide, hydrogen and nitrogen coming from the conversion section 4 of carbon monoxide and fed to the carbamate synthesis section 24 comprised between 10% and 50%, preferably 30% and 45% of the total raw ammonia synthesis gas flow coming from the carbon monoxide conversion section 4.

Analogously, particularly satisfying results have been obtained with the flow coming from the ammonia synthesis section 8 (means 27) corresponding to a portion comprised between 10 and 50%, preferably between 30 and 45% of the total flow comprising ammonia, hydrogen and nitrogen obtained in the ammonia synthesis section 8.

By increasing the production capacity of ammonia and urea plants and at the same time by drawing the additional amount of the reactants from the gas flow directed to the existing decarbonation section as shown in the example of FIG. 2, it may be advantageous, instead of excessively overloading the existing sections upstream of the carbonation section (in particular section 3), to provide an additional section for the production of raw ammonia synthesis gas comprising carbon monoxide, hydrogen and nitrogen.

Advantageously, the method of modernisation according to the present invention foresees therefore the further step of providing an additional section 35 for the production of raw ammonia synthesis gas comprising carbon monoxide, hydrogen and nitrogen and means 36 for feeding a raw ammonia synthesis gas flow comprising carbon monoxide, hydrogen and nitrogen obtained in the additional section 35 to the conversion section of carbon monoxide.

The example of FIG. 2 is based on the assumption that, generally speaking, the carbon monoxide conversion section 4 is able to stand even remarkable increases of load. Anyway, nothing prevents from providing a further conversion section of carbon monoxide (not shown), preventing the additional raw ammonia synthesis gas flow from passing through the section 4.

The section 35 for the production of raw ammonia synthesis gas comprising carbon monoxide, hydrogen and nitrogen, may comprise one or more reforming steps or, preferably, a step of partial catalytic oxidation.

The additional flow of carbon monoxide, hydrogen and nitrogen is obtained by feeding a flow comprising hydrocarbons and a flow comprising nitrogen, for example air and preferably air enriched in oxygen to the section 35 through means 37, respectively 38.

It is worth noting how the present invention may advantageously be implemented, independently from how the additional flow of carbon dioxide, hydrogen and nitrogen to be delivered to the carbamate synthesis section 24 is obtained.

Figure 3:
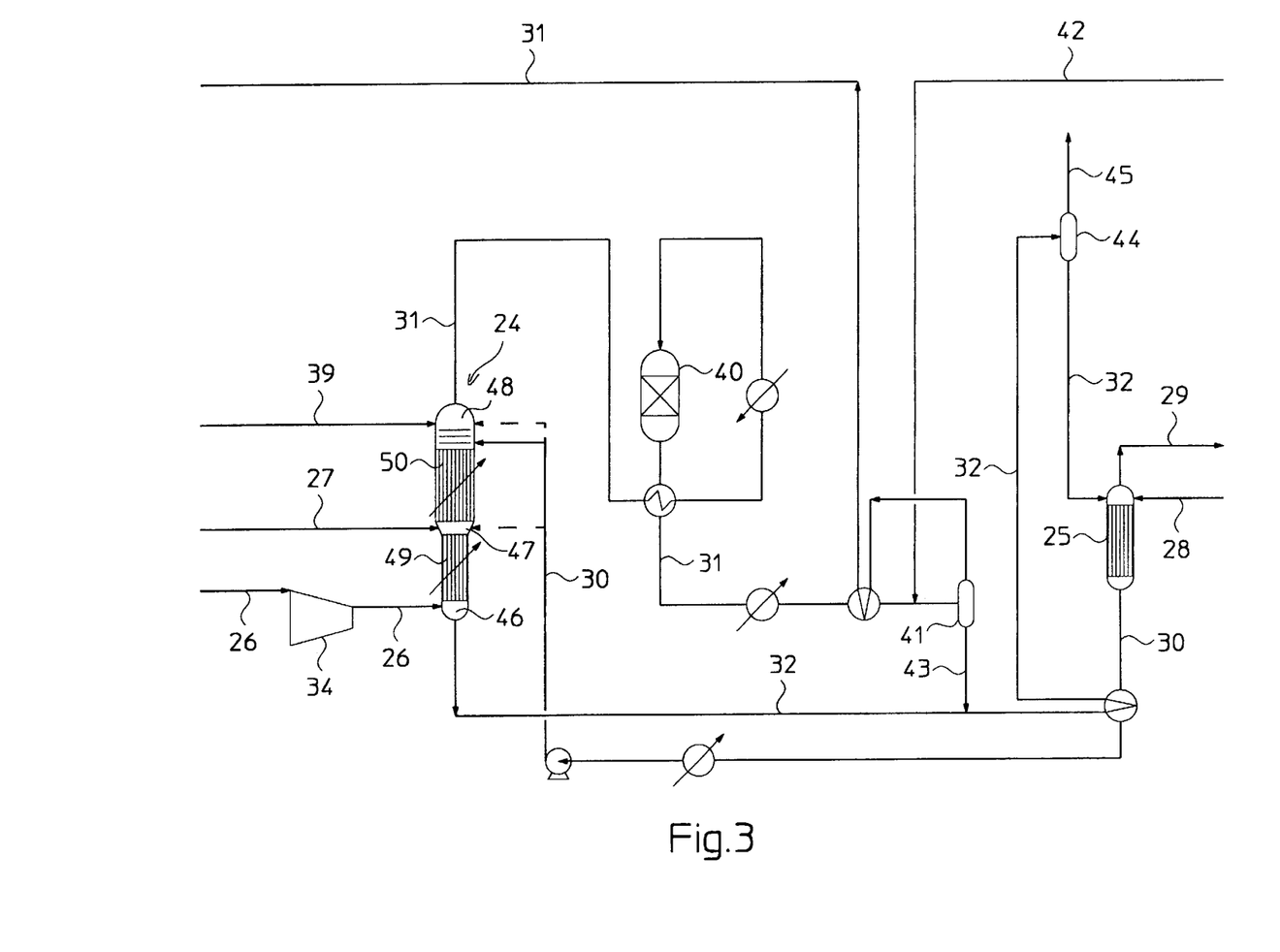
FIG. 3 schematically shows a detail of the plant according to the invention represented by the block diagram of FIG. 2.

The details relative to the additions and modifications brought with the present method of modernisation are better highlighted with reference to FIG. 3.

In FIG. 3, the details of the plant for the simultaneous production of ammonia and urea which are structurally and functionally equivalent to those illustrated in FIG. 2 will be indicated with the same reference numerals and will not be described any more.

Just in order to simplify the disclosure of the present invention, in FIG. 3 only a portion of the plant for the combined production of ammonia and urea of FIG. 2 is schematically illustrated, the sections left out being not significant for the comprehension of the present invention.

Furthermore, specific reference to the connecting ducts of the various parts of the plant described in the following and illustrated in FIG. 3 will be made only when strictly necessary. These ducts are per se conventional.

In FIG. 3, means are indicated with 39 for feeding a flow comprising water coming from a concentration section (not shown) of the urea plant to the carbamate synthesis section 24.

Such feed (that is absolutely optional) is advantageous whenever an amount of water is required in the carbamate synthesis section 24 which is greater than that contained in the flow comprising diluted carbamate in aqueous solution coming from the decomposition section 25 (means 30).

In doing so, the delivery to the section 24 of a flow comprising water coming from outside the process is avoided, recycling the water obtained in one of the sections downstream of the urea synthesis reactor and thus obtaining saving in the operation costs.

According to an advantageous embodiment of the present invention, means 27 between the ammonia synthesis section 8 and the carbamate synthesis section 24 are provided, in order to delivery to the latter a flow comprising ammonia in vapour phase that immediately reacts with the carbon dioxide present in the section 24, enhancing the carbamate synthesis.

Before being introduced in the ammonia synthesis section 8, it may be preferable to suitably purify the gas flow comprising hydrogen and nitrogen flowing through the means 31. To this end, in FIG. 3, suitable conventional apparatuses for the methanation (40) and drying (41) of such flow are shown.

In particular, in the drying apparatus 41 the gas flow comprising hydrogen and nitrogen is dehydrated by washing it with liquid ammonia so as to remove possible traces of water.

In this respect, a flow comprising liquid ammonia leads into the means 31 through the means 42 and is thus fed to the drying apparatus 41 together with the gas flow comprising hydrogen and nitrogen.

In such apparatus, the water present in the gas flow is absorbed by the ammonia obtaining an aqueous solution of ammonia that is advantageously recycled through the means 43 and 32 to the section 25, while the gas flow comprising hydrogen and nitrogen free of water is fed to the ammonia synthesis section 8 through means 31.

In the example of FIG. 3, a separator 44 is also provided between the carbamate synthesis section 24 and the carbamate decomposition section 25, for extracting—through means 45—from the flow of carbamate in aqueous solution possible entrainments of hydrogen and nitrogen.

The carbamate decomposition section 25 can comprise a decomposition unit (for example a stripper) as shown in FIG. 3, or two or more decomposition units provided in series which operate at different temperature and pressure conditions.

Preferably, in the example of FIG. 3, the single decomposition unit operates at temperature and pressure conditions analogous to those present in the urea synthesis section 10.

In turn, the carbamate synthesis section 24 may comprise a single reaction chamber into which the means 26, 27 and 30 leads, or several reaction chambers disposed in respective apparatuses or in a single apparatus as in the example illustrated in FIG. 3.

In this case, the section 24 comprises three chambers 46, 47 and 48 separated by two absorbers 49 and 50, for example of the film type.

The first chamber 46 is provided in correspondence of a bottom end of the section 24 and is in fluid communication with the means 26 for feeding the gas flow comprising hydrogen, nitrogen and carbon dioxide to such section, respectively with the means 32 for feeding the flow comprising carbamate in aqueous solution obtained in the section 24 to the carbamate decomposition section 25.

The second chamber 47 is provided in a central area of the section 24 and is in fluid communication with the means 27 for feeding a flow comprising ammonia, hydrogen and nitrogen coming from the ammonia synthesis section 8.

The third chamber 48 is provided in correspondence of a top end of the section 24 and is in fluid communication with the means 39 and 30 for feeding a flow comprising water, respectively diluted carbamate in aqueous solution, and with the means 31 for feeding a gas flow comprising hydrogen and nitrogen obtained in the carbamate synthesis section 24 to the ammonia synthesis section 8.

The first absorber 49 is provided between the first and second chamber 46 and 47 and comprises, for example, a plurality of pipes having opposed ends in fluid communication with the first, respectively second chamber.

The second absorber 50 is provided between the second and third chamber 47, 48 and comprises, for example, a plurality of pipes having opposed ends in fluid communication with the second, respectively third chamber.

Thanks to a so designed carbamate synthesis section 24, it is possible to obtain a fast and effective reaction between ammonia and carbon dioxide in a structurally simple device of limited dimensions and low manufacture and operation costs.

The flow comprising diluted carbamate in aqueous solution coming from the carbamate decomposition section 25 is preferably fed to the third chamber 48—through the means 30—proximate to the second absorber 50.

Moreover, satisfying results have been obtained by feeding such flow comprising diluted carbamate in aqueous solution to the third chamber 48 proximate to the upper end of the section 24, or to the second chamber 47 proximate to the second absorber 50 as indicated in FIG. 3 by the dashed lines.

Advantageously, the third chamber 48—that operates preferably in adiabatic conditions—comprises a plurality of perforated horizontal trays of conventional type that allow to increase the absorption yield.

According to the specific structure of the carbamate synthesis section 24 of FIG. 3, the flow comprising hydrogen, nitrogen and carbon dioxide is fed—through the duct 26—to the first chamber 46.

From the chamber 46 such flow is made to enter—on the tubes side—in the first absorber 49 wherein it flows in countercurrent with a flow comprising ammonia and carbamate in aqueous solution coming from the second chamber 47.

In this area, a major portion of the carbon dioxide reacts with free ammonia—preferably both in vapour phase and in liquid phase—forming carbamate that collects in the chamber 46.

The gas flow coming out from the first absorber 49 mixes—in the chamber 47—with the flow of ammonia, hydrogen and nitrogen coming from the ammonia synthesis section 8 through the means 27, and enters—on the tubes side—in the second absorber 50 where a major portion of carbon dioxide and ammonia in vapour phase is absorbed in a diluted ammoniacal solution coming from the third chamber 48.

The third chamber 48, that is fed through the means 39 and 30 by a flow comprising water coming from the urea concentration section, respectively by a flow comprising carbamate in aqueous solution coming from the carbamate decomposition section 25, permits the final removal of the residual ammonia and carbon dioxide.

Thanks to the present invention, it is possible, for example, to obtain a gas flow comprising hydrogen and nitrogen in outlet from the third chamber 48 (means 31), with a molar content of residual ammonia equal to about 1% and a molar content of residual carbon dioxide equal to about 0.05%.

The reaction heat which is developed in the carbamate synthesis section 24, is advantageously removed by indirect heat exchange with a cooling fluid (for example water) which is preferably made to pass in the absorbers 49 and 50 on the shell side.

In this way it is possible to maintain the temperature inside the carbamate synthesis section 24 in a range wherein the carbamate crystallisation inside the pipes of the absorbers is avoided.

For example, temperature and pressure values inside the carbamate synthesis section 24 are comprised between 140–200 abs bar (preferably 180 abs bar), respectively 110–150° C. (preferably 130° C.).

The plant for the combined production of ammonia and urea obtained through the method of modernisation according to this invention, may also be advantageously realised ex-novo.

Such plant will comprise the sections and the means described with reference to FIG. 2. The features of the plant for ammonia and urea production are reported and claimed in the enclosed claims 17–22.

The advantages described with reference to the simultaneous modernisation of the existing plants for ammonia and urea production are all present in the plant realised ex-novo, with the only exception of the investment costs, which are clearly much higher for a new plant.

Thanks to the plant according to the present invention, either obtained through the above described method of modernisation or realised ex-novo, it is advantageously possible to implement the process for the simultaneous production of ammonia and urea described and claimed in the enclosed claims 7–15.

EXAMPLE

The assumption is made, to be willing to modernise at the same time a plant for ammonia production and a plant for urea production, whose existing sections cannot be enlarged or further developed with the conventional methods. Essentially, such modernisation is intended to increase the capacity of those plants.

The increase of capacity is so defined:—$NH_3$ plant: from 1300 MTD $NH_3$ to 2000 MTD $NH_3$;—urea plant from 2300 MTD urea to 3500 MTD urea.

Thanks to this invention it is advantageously possible to obtain the missing capacities (700 MTD $NH_3$ and 1200 MTD urea) by suitably integrating the two productions, only with respect to the required additional capacities, without bringing substantial modifications to the existing plants.

In this example, two different kinds of plant for urea synthesis are considered, whereas the plant for ammonia synthesis is always of the same type:

case 1: the urea plant is based on the stripping process with $CO_2$;

case 2: the urea plant is based on the self-stripping process (with ammonia).

Case 1: the operational conditions in the synthesis section of urea (synthesis reactor) are as follows pressure: ≡140÷150 abs bar temperature: 183÷188° C.

mol. $NH_3/CO_2$: ≡3 mol. $H_2O/CO_2$: ≡0.5

η: 60% (yield conversion)

The solution of urea coming out from the synthesis reactor is stripped in a conventional manner in a stripper, using feed $CO_2$ as stripping agent. The vapours so obtained are partially condensed in a carbamate condenser and supplied to the synthesis reactor together with the recycled aqueous solution of carbamate coming from the urea recovery section.

The simultaneous modernisation of the ammonia plant and of the urea plant just described according to the method of the present invention, allows to achieve a productive capacity of the urea plant of 3500 MTD. Furthermore, the operational conditions in the urea synthesis section were as follows:

pressure: ≡140÷150 abs bar temperature: 185÷189° C.

mol. $NH_3/CO_2$: ≡3 mol. $H_2O/CO_2$: ≡0.15

η: 65% (yield conversion)

Advantageously, apart from a remarkable increase in capacity, it was possible to increase the yield from 60% to 65% thanks to the decrease of the $H_2O/CO_2$ molar ratio from 0.5% to 0.15% with ensuing savings in terms of energy consumption.

Case 2: the operational conditions in the synthesis section of urea (synthesis reactor) are as follows.

pressure: ≡140÷150 abs bar temperature: 185÷190° C.

mol. $NH_3/CO_2$: ≡3.2 mol. $H_2O/CO_2$: ≡0.5

η: 62% (yield conversion)

The solution of urea coming out from the synthesis reactor is stripped in a conventional way in a stripper, according to self-stripping conditions. The vapours so obtained are condensed in a first condenser and recycled to the reactor. The solution of urea coming out from the stripper is in turn distilled at 18 abs. bar in a medium pressure step and at 4 abs. bar in a low pressure step and is passed on to the vacuum concentration section, so as to obtain 99.7% Wt. fused urea . The vapours rich in ammonia coming out from the medium pressure distillation section are partially condensed in a second condenser in presence of a recycled aqueous solution of carbamate and are passed on to a rectifying column: the head product is pure $NH_3$, that upon condensation, is recycled to the reactor; the bottom product is an aqueous solution of carbamate that is sent to the first condenser and hence to the reactor.

The simultaneous modernisation just described of the ammonia plant and of the urea plant according to the method of the present invention, allows to achieve a productive capacity of urea plant of 3500 MTD. Furthermore, the operational conditions in the urea synthesis section are as follows pressure: ≡140÷150 abs bar
temperature: 185÷190° C.
mol. $NH_3/CO_2$: ≡3.2
mol. $H_2O/CO_2$: ≡0.2
η: 65% (yield conversion)

In this case as well, beside the increase of production capacity, an increase of the yield conversion was advantageously encountered, to full advantage of lower energy consumption.

What is claimed is:

1. Method for the simultaneous modernisation of a plant for ammonia production and a plant for urea production, the plant for ammonia production comprising a section for the production of raw ammonia synthesis gas comprising carbon monoxide, hydrogen and nitrogen, a carbon monoxide conversion section, a decarbonation section, a methanation section, a compression section of the ammonia synthesis gas and an ammonia synthesis section, provided in series, the plant for urea production comprising a compression section of carbon dioxide, a urea synthesis section and a urea recovery section, said method being characterised in that it comprises the steps of:

providing a carbamate synthesis section and a carbamate decomposition section;

providing means for feeding a compressed raw ammonia synthesis gas flow comprising carbon dioxide, hydrogen and nitrogen to said carbamate synthesis section;

providing means for feeding a portion of a flow comprising ammonia, hydrogen and nitrogen obtained in said ammonia synthesis section to said carbamate synthesis section;

providing means for feeding at least part of a flow comprising carbamate in aqueous solution coming from said urea recovery section to said carbamate decomposition section;

providing means for feeding a flow comprising ammonia and carbon dioxide in vapour phase obtained in said decomposition section to said urea synthesis section;

providing means for feeding a flow comprising diluted carbamate in aqueous solution obtained in said carbamate decomposition section to said carbamate synthesis section;

providing means for feeding a gas flow comprising hydrogen and nitrogen obtained in said carbamate synthesis section to said ammonia synthesis section;

providing means for feeding a flow comprising carbamate in aqueous solution obtained in said carbamate synthesis section to said carbamate decomposition section and/or to said urea synthesis section.

2. Method according to claim 1, characterised in that it further comprises the steps of:

providing an additional compression section;

providing means for feeding said raw ammonia synthesis gas flow comprising carbon dioxide, hydrogen and nitrogen to said additional compression section and from this to said carbamate synthesis section.

3. Method according to claim 1, characterised in that said means for feeding said raw ammonia synthesis gas flow comprising carbon dioxide, hydrogen and nitrogen, to said carbamate synthesis section comprises means for drawing a portion of a raw ammonia synthesis gas flow coming from said conversion section of carbon monoxide and directed to said decarbonation section.

4. Method according to claim 3, characterised in that it further comprises the steps of:

providing an additional section for producing raw ammonia synthesis gas comprising carbon monoxide, hydrogen and nitrogen;

providing means for feeding a raw ammonia synthesis gas flow comprising carbon monoxide, hydrogen and nitrogen, obtained in said additional section to said conversion section of carbon monoxide.

5. Method according to claim 1, characterised in that said carbamate synthesis section comprises:

a first chamber in fluid communication with said means for feeding the raw ammonia synthesis gas flow comprising hydrogen, nitrogen and carbon dioxide to said carbamate synthesis section, respectively with said means for feeding the flow comprising carbamate in aqueous solution obtained in said carbamate synthesis section to said carbamate decomposition section and/or to said urea synthesis section;

a second chamber in fluid communication with said means for feeding the flow comprising ammonia, hydrogen and nitrogen obtained in said ammonia synthesis section to said carbamate synthesis section;

a third chamber in fluid communication with said means for feeding the flow comprising diluted carbamate in aqueous solution to said carbamate synthesis section, respectively with said means for feeding the gas flow comprising hydrogen and nitrogen obtained in said carbamate synthesis section to said ammonia synthesis section;

a first absorber film provided between said first and said second chamber and comprising a plurality of pipes having opposed ends in fluid communication with said first and second chamber respectively;

a second absorber film provided between said second and said third chamber and comprising a plurality of pipes having opposed ends in fluid communication with said second and third chamber respectively.

6. Method according to claim 1, characterised in that it further comprises the step of:

providing means for feeding a flow comprising water coming from a urea concentration section to said carbamate synthesis section.

7. Process for the simultaneous production of ammonia and urea in a plant of the type comprising a section for the production of raw ammonia synthesis gas comprising carbon monoxide, hydrogen and nitrogen, a carbon monoxide conversion section, a decarbonation section, a methanation section, a compression section for the ammonia synthesis gas, an ammonia synthesis section, a carbon dioxide compression section, a urea synthesis section and a urea recovery section, the process being characterised in that a first portion of ammonia and urea is produced through the steps of:

flowing a flow of raw ammonia synthesis gas comprising carbon dioxide, hydrogen and nitrogen through said sections of decarbonation, methanation and compression of the synthesis gas, obtaining a compressed gas flow comprising hydrogen and nitrogen;

feeding said suitably compressed gas flow comprising hydrogen and nitrogen to said ammonia synthesis section;

feeding a portion of the ammonia obtained in said ammonia synthesis section together with the carbon dioxide coming out of said decarbonation section to said urea synthesis section;

whereas a second portion of ammonia and urea is produced through the steps of:

submitting at least part of a flow comprising carbamate in aqueous solution coming from said urea recovery section to a treatment of partial decomposition in a carbamate decomposition section, thus obtaining a flow comprising ammonia and carbon dioxide in vapour phase and a flow comprising diluted ceLrbamate in aqueous solution;

feeding said flow comprising ammonia and carbon dioxide in vapour phase to said urea synthesis section;

feeding said flow comprising diluted carbamate in aqueous solution resulting from said step of treatment to a carbamate synthesis section;

feeding a suitably compressed raw ammonia synthesis gas flow comprising carbon dioxide, hydrogen and nitrogen to said carbamate synthesis section;

feeding a portion of a flow comprising ammonia, hydrogen and nitrogen obtained in said ammonia synthesis section to said carbamate synthesis section;

reacting said ammonia with said carbon dioxide in said carbamate synthesis section, obtaining a flow comprising carbamate in aqueous solution and a gas flow comprising hydrogen and nitrogen;

feeding said flow comprising carbamate in aqueous solution to said carbamate decomposition section and/or to said urea synthesis section;

feeding said gas flow comprising hydrogen and nitrogen to said ammonia synthesis section.

8. Process according to claim 7, characterised in that it further comprises the step of:

subjecting to compression said raw ammonia synthesis gas flow comprising carbon dioxide, hydrogen and nitrogen in an additional compression section before to being fed to said carbamate synthesis section.

9. Process according to claim 7, characterised in that said raw ammonia synthesis gas flow comprising carbon dioxide, hydrogen and nitrogen fed to said carbamate synthesis section comprises a portion of a raw ammonia synthesis gas flow coming out from said conversion section of carbon monoxide and directed to said decarbonation section.

10. Process according to claim 9, characterised in that it further comprises the steps of:

subjecting to combustion a hydrocarbons flow thus obtaining an additional raw ammonia synthesis gas flow comprising carbon monoxide, hydrogen and nitrogen;

feeding said additional raw ammonia synthesis gas flow comprising carbon monoxide, hydrogen and nitrogen from said combustion section of the hydrocarbons to said conversion section of carbon monoxide.

11. Process according to claim 7, characterised in that said flow coming from said ammonia synthesis section comprises ammonia in vapour phase.

12. Process according to claim 7, characterised in that said flow coming from said ammonia synthesis section is a portion comprised between 10% and 50% of the total flow comprising ammonia, hydrogen and nitrogen obtained in said ammonia synthesis section.

13. Process according to claim 12, characterised in that said flow coming from said ammonia synthesis section is a portion comprised between 30% and 45% of the total flow comprising ammonia, hydrogen and nitrogen obtained in said ammonia synthesis section.

14. Process according to claim 9, characterised in that the portion of the raw ammonia synthesis gas flow comprising carbon dioxide, hydrogen and nitrogen coming from said carbon monoxide conversion section and fed to said carbamate synthesis section is comprised between 10% and 50% of the total raw ammonia synthesis gas flow coming from said carbon monoxide conversion section.

15. Process according to claim 14, characterised in that the portion of the raw ammonia synthesis gas flow comprising carbon dioxide, hydrogen and nitrogen coming from said carbon monoxide conversion section is comprised between 30% and 45% of the total raw ammonia synthesis gas flow coming from said carbon monoxide conversion section.

16. Process according to claim 7, characterised in that it further comprises the step of feeding a flow comprising water coming from a urea concentration section to said carbamate synthesis section.

17. Plant for the simultaneous production of ammonia and urea comprising:

a section for the production of raw ammonia synthesis gas comprising carbon monoxide, hydrogen and nitrogen, a carbon monoxide conversion section, a decarbonation section, a methanation section, a compression section for the ammonia synthesis gas, an ammonia synthesis section, a carbon dioxide compression section, a urea synthesis section, a urea recovery section, a carbamate synthesis section and a carbamate decomposition section;

means for feeding a compressed raw ammonia synthesis gas flow comprising carbon dioxide, hydrogen and nitrogen to said carbamate synthesis section;

means for feeding a portion of a flow comprising ammonia, hydrogen and nitrogen obtained in said ammonia synthesis section to said carbamate synthesis section;

means for feeding at least part of a flow comprising carbamate in aqueous solution coming from said urea recovery section to said carbamate decomposition section;

means for feeding a flow comprising ammonia and carbon dioxide in vapour phase obtained in said decomposition section to said urea synthesis section;

means for feeding a flow comprising diluted carbamate in aqueous solution obtained in said carbamate decomposition section to said carbamate synthesis section;

means for feeding a gas flow comprising hydrogen and nitrogen obtained in said carbamate synthesis section to said ammonia synthesis section;

means for feeding a flow comprising carbamate in aqueous solution obtained in said carbamate synthesis section to said carbamate decomposition section and/or to said urea synthesis section.

18. Plant according to claim 17, characterised in that it further comprises:

an additional compression section;

means for feeding said raw ammonia synthesis gas flow comprising carbon dioxide, hydrogen and nitrogen to said additional compression section and from this to said carbamate synthesis section.

19. Plant according to claim 17, characterised in that said means for feeding said raw ammonia synthesis gas flow comprising carbon dioxide, hydrogen and nitrogen, to said carbamate synthesis section comprises means for drawing a portion of a raw ammonia synthesis gas flow coming from said carbon monoxide conversion section and directed to said decarbonation section.

20. Plant according to claim 19, characterised in that it further comprises:

an additional section for producing raw ammonia synthesis gas comprising carbon monoxide, hydrogen and nitrogen;

means for feeding a raw ammonia synthesis gas flow comprising carbon monoxide, hydrogen and nitrogen, obtained in said additional section to said carbon monoxide conversion section.

21. Plant according to claim 17, characterised in that said carbamate synthesis section comprises:

a first chamber in fluid communication with said means for feeding the raw ammonia synthesis gas flow comprising hydrogen, nitrogen and carbon dioxide to said carbamate synthesis section, respectively with said means for feeding the flow comprising carbamate in aqueous solution obtained in said carbamate synthesis section to said carbamate decomposition section and/or to said urea synthesis section;

a second chamber in fluid communication with said means for feeding the flow comprising ammonia, hydrogen and nitrogen obtained in said ammonia synthesis section to said carbamate synthesis section;

a third chamber in fluid communication with said means for feeding the flow comprising diluted carbamate in aqueous solution to said carbamate synthesis section, respectively with said means for feeding the gas flow comprising hydrogen and nitrogen obtained in said carbamate synthesis section to said ammonia synthesis section;

a first absorber film provided between said first and said second chamber and comprising a plurality of pipes having opposed ends in fluid communication with said first and second chamber respectively;

a second absorber film provided between said second and said third chamber and comprising a plurality of pipes having opposed ends in fluid communication with said second and third chamber respectively.

22. Plant according to claim 17, characterised in that it further comprises:

means for feeding a flow comprising water to said carbamate synthesis section, in fluid communication with an urea concentration section.

* * * * *